United States Patent [19]

Bregnedal et al.

[11] 4,384,140
[45] May 17, 1983

[54] 2-CHLOROETHYL UREA DERIVATIVES

[75] Inventors: Peter Bregnedal, Allerød; Jørn L. M. Buus, Bjaeverskov, both of Denmark

[73] Assignee: Kefalas A/S, Copenhagen-Valby, Denmark

[21] Appl. No.: 348,724

[22] Filed: Feb. 16, 1982

Related U.S. Application Data

[62] Division of Ser. No. 191,910, Sep. 29, 1980.

[30] Foreign Application Priority Data

Oct. 3, 1979 [GB] United Kingdom ............... 7934306

[51] Int. Cl.³ .......................................... C07C 127/17
[52] U.S. Cl. ....................................... 564/56; 564/47; 564/57
[58] Field of Search ........................... 564/47, 56, 57

[56] References Cited

PUBLICATIONS

Saikawa et al., CA 90:54978b, (1979).
Hori et al., CA 91:211367s, (1980).
Nakas et al., CA 79:53186c, (1973).

Primary Examiner—Thomas A. Waltz
Attorney, Agent, or Firm—Gordon W. Hueschen

[57] ABSTRACT

The present invention relates to novel aminoalkyl substituted nitrosourea derivatives as well as their acid addition salts with pharmaceutically acceptable acids showing pronounced antineoplastic effectiveness in animal experiments.

The novel compounds of the present invention may be represented by the following formula:

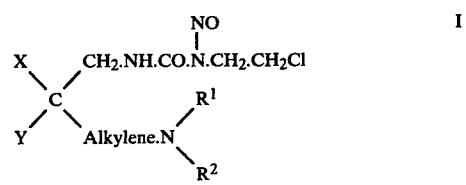

wherein X and Y are the same or different, and are selected from the group consisting of a phenyl group and a cyclohexyl group, said phenyl and cyclohexyl groups being optionally substituted with one or two substituents selected from a halogen atom, a lower alkyl group having from one to four carbon atoms inclusive, a trifluore methyl group, a cyano group, a phenyl group, a cyclohexyl group and a lower alkyloxy group having from one to four carbon atoms inclusive.

"Alkylene" is an alkylene group, branched or unbranched, having from one to four carbon atoms inclusive, and $R^1$ and $R^2$ are the same or different, and are each selected from the group consisting of lower alkyl groups having from one to four carbon atoms inclusive, and benzyl groups, or they form together with the nitrogen atom a saturated five- or six-membered heterocyclic ring, such as a pyrrolidine, piperidine, morfoline, thiomorfoline, or N-lower-alkyl-piperazine ring, said heterocyclic ring being optionally substituted with lower alkyl groups having from one to four carbon atoms inclusive, as well as pharmaceutically acceptable acid addition salts thereof.

6 Claims, No Drawings

2-CHLOROETHYL UREA DERIVATIVES

This is a divisional of application Ser. No. 191,910, filed Sept. 29, 1980.

BACKGROUND OF THE INVENTION

In recent years the compounds 1-(2-Chloroethyl)-3-cyclohexyl-1-nitrosourea (lomustine, CCNU) and 1,3-bis(2-chloroethyl)-1-nitrosourea (BCNU) have been found effective as cytostatic agents in the treatment of various tumors, either alone or in combination with other cytostatic drugs.

Unfortunately, they also have serious untoward side effects and are rather toxic compounds, and the therapeutic index, the ratio between the toxic dose and the therapeutic dose, is not very favorable.

SUMMARY OF THE INVENTION

According to the present invention it has now surprisingly been found that the compounds of Formula I, as well as their acid addition salts in animal experiments show cytostatic effects comparable to BCNU and, at the same time, less toxicity.

Based upon the animal experiments the preferred compounds of this invention are those of Formula I, in which X and Y are unsubstituted phenyl groups or phenyl groups having fluorine atoms at the para-position, "Alkylene" is a trimethylene group, optionally substituted with a methyl group in the 2-position, and $R^1$ and $R^2$ are methyl groups.

The present invention also includes pharmaceutically acceptable acid addition salts of the compounds of Formula I. Such salts are easily prepared by methods known to the art.

The base is reacted with either the calculated amount of organic or inorganic acid in an aqueous miscible solvent, such as acetone or methanol, with isolation of the salt by concentration and cooling or an excess of the acid in aqueous immiscible solvent, such as ethyl ether or methylene chloride, with the desired salt separating directly. Exemplary of such organic salts are those with maleic, fumaric, benzoic, ascorbic, embonic (pamoic), succinic, oxalic, bis-methylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, flutamic, benzene sulfonic and theophylline acetic acids as well as the 8-halotheophyllines, for example 8-bromotheophylline. Exemplary of inorganic salts of the compounds of Formula I are those with hydrochloric, hydrobromic, sulfuric, sulfamic, phosphoric and nitric acids. Of course, these salts may also be prepared by the classical method of double decomposition of appropriate salts which is wellknown to the art.

The compounds of Formula I and the non-toxic acid addition salts thereof may be administered both orally and parenterally, for example in the form of tablets, capsules, powders, syrups or solutions for injection.

The present invention moreover comprises a method for the preparation of the novel nitrosourea derivatives of Formula I whereby a compound of the following formula:

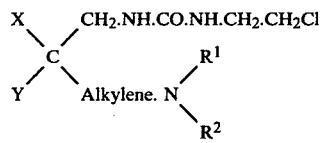

wherein X, Y, $R^1$, $R^2$ and "Alkylene" are as defined above, is nitrosated in acid medium to yield the compound of Formula I which is isolated either as the free base or in the form of a pharmaceutically acceptable acid addition salt thereof.

The nitrosation may according to the invention preferably be carried out in well-known manner by using sodiumnitrite in acid medium, such as formic acid solution, hydrochloric acid solution, glacial acetic solution, or the like. Sometimes it has been found advantageous to use the $NO_2^-$-anion formed by reduction of the $NO_3^-$-anion in situ by means of copper in for example glacial acetic acid solution.

The starting materials of Formula II are also novel compounds and form part of this invention. They may according to the invention conveniently be prepared according to the following scheme:

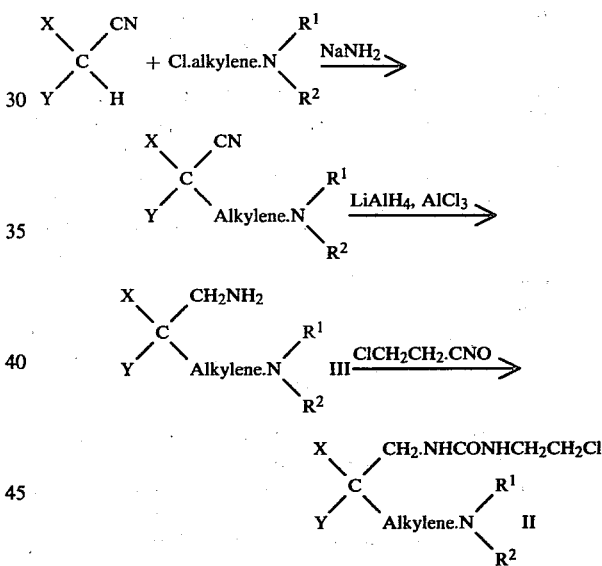

In all these reactions are X, Y, $R^1$, $R^2$ and "Alkylene" as defined above.

The preparation of some of the compounds of Formula III is described in German Pat. No. 2438965, and others may be prepared in analogous manner.

The following examples are given to illustrate the method of the present invention but, they are to be understood as exemplary only and are not to be construed as limiting.

EXAMPLE 1

N-(2-Chloroethyl)-N'-(2,2-bis(4-fluorophenyl)-5-(dimethylamino)pentyl)-N-nitrosourea and its oxalate (LU16-035).

The starting material, N-(2-Chloroethyl)-N'-(2,2-bis(4-fluorophenyl)-5-(dimethylamino)pentyl)urea, was prepared in the following way:

112 Grams 0.5 mole of bis-(4-fluorophenyl)acetonitrile were dissolved in dry toluene and 50 grams of a 50% suspension of sodamide in toluene were added at once while stirring, whereupon 70 grams of 3-chloro-N,N-dimethylpropylamine were added, and the reaction mixture was warmed to 60 degrees Centigrade, where a reaction started causing a rise in temperature to 90 degrees centigrade, at which temperature the reaction mixture was kept for 30 minutes. The reaction mixture was poured into 1 liter of crushed ice. The aqueous phase was separated off and extracted twice with 250 milliliters of 2 N hydrochloric acid. The combined aqueous phases were made alkaline with sodium hydroxide solution (28%), the base which separated out was extracted with methylene chloride, the methylene chloride solution dried over anhydrous magnesium sulfate, evaporated and distilled. The fraction obtained at 165-175 degrees centigrade/0.2 mmHg consisted of almost pure 2,2-bis-(4-fluorophenyl)-5-(dimethylamino)pentanenitrile. Yield: 129 grams.

25 Grams of lithium aluminum hydride were suspended in 500 milliliters of diethyl ether and 82 grams of anhydrous aluminum chloride in 250 milliliters of diethyl ether added, whereupon a solution of 125 grams of the nitrile in 250 milliliters of diethyl ether was added dropwise while stirring during 30 minutes under reflux. The reaction mixture was boiled under reflux for further 3 hours and hydrolysed by adding 500 milliliters of sodium hydroxide solution (28%) dropwise over 30 minutes. The etherphase was decanted and the residue washed twice with 500 milliliters of diethyl ether. The combined etherphases were extracted twice with 250 milliliters of 2 N hydrochloric acid and the combined aqueous phases made alkaline to pH 10 with sodium hydroxide solution (28%). The base which separated out was extracted with 1000 milliliters of diethyl ether, the ether solution dried over anhydrous magnesium sulfate and evaporated on a heating bath at 50 degrees centigrade. The residue was dissolved in 500 ml acetone/ethanol, 99% (1:1), and oxalic acid was added until pH 3. By standing at zero degrees centigrade 50 grams of the oxalate of $N^5,N^5$-dimethyl-2,2-bis(4-fluorophenyl)-1,5-pentanediamine crystallized out. M.P.: 85-87 degrees centigrade.

30 Grams of this oxalate were dissolved in 100 milliliters of water, the solution made alkaline to pH 10 with sodium hydroxide (28%), and the base which separated out extracted twice with 100 milliliters of methylene chloride. The combined methylene chloride phases were dried over anhydrous magnesium sulfate, filtered and to the resulting solution were added dropwise at zero degrees centigrade and while stirring 10 grams of 2-chloroethyl isocyanate, whereupon the stirring was continued for further 30 minutes. The precipitate which crystallized out consisted of 22 grams of N-(2-chloroethyl)-N'-(2,2-bis(4-fluorophenyl)-5-(dimethylamino)pentyl)urea melting at 205-210 degrees centigrade after washing with diethyl ether.

13.6 Grams of this substance were dissolved in 100 milliliters of 2 N hydrochloric acid, the solution cooled to zero degrees centigrade, and a solution of 4 grams of sodium nitrite in 15 milliliters of water added dropwise at 0-5 degrees centigrade, whereupon the solution was stirred for further 30 minutes at zero degrees centigrade. 100 Milliliters of methylene chloride were added, solid sodium carbonate added to pH 8, and the reaction mixture stirred for further 30 minutes at zero degrees centigrade. The methylene chloride phase was separated, dried over anhydrous magnesium sulfate and evaporated at 20 degrees centigrade. The resulting oil was dissolved in 100 milliliters of acetone and oxalic acid added to pH 3. The resulting solution was left standing at zero degrees centigrade and the resulting crystals sucked off. The crystals were dissolved in boiling methanol, and after cooling were added 100 milliliters of dry diethyl ether.

By standing and cooling at zero degrees centigrade 6.9 grams of the oxalate of N-(2-chloroethyl)-N'-(2,2-bis(4-fluorophenyl)-5-(dimethylamino)pentyl)-N-nitrosourea were obtained as white crystals melting at 144-145 degrees centigrade.

EXAMPLE 2

N-(2-chloroethyl)-N'-(2,2-diphenyl-5-(dimethylamino)-pentyl)-N-nitrosourea and its oxalate (LU15-132).

The starting material, N-(2-chloroethyl)-N'-(2,2-diphenyl-5-(dimethylamino)pentyl)urea, was prepared in the following way:

170 Grams of $N^5,N^5$-dimethyl-2,2-diphenyl-1,5-pentanediamine were dissolved in 500 milliliters of methylene chloride and the solution cooled to zero degrees centigrade in a cooling bath. 70 Grams of 2-chloroethyl isocyanate were then added dropwise at this temperature and the reaction mixture stirred at 30 minutes. The mixture was then evaporated at 50 degrees centigrade, the residue dissolved in 500 milliliters ethyl acetate/diisopropyl ether (1:1). By standing and cooling at zero degrees centigrade 150 grams of N-(2-chloroethyl)-N'-(2,2-diphenyl)-5-(dimethylamino)pentyl)urea were obtained as white crystals melting at 110-112 degrees centigrade.

23.2 Grams of the thus obtained urea-derivative were nitrosated with 6.9 grams of sodium nitrite in hydrochloric acid solution as described in Example 1, and 20 grams of the oxalate of N-(2-chloroethyl)-N'-(2,2-diphenyl-5-(dimethylamino)pentyl)-N-nitrosourea were obtained as white crystals melting at 138-140 degrees centigrade.

EXAMPLE 3

N-(2-chloroethyl)-N'-(2,2-diphenyl-4-methyl-5-(dimethylamino)pentyl)-N-nitrosourea (LU16-022).

The starting material, N-(2-chloroethyl)-N'-((2,2-diphenyl)-4-methyl-5-(dimethylamino)-pentyl)urea, was prepared in the following way:

118 Grams of $N^5,N^5$-dimethyl-2,2-diphenyl-4-methyl-1,5-pentanediamine were dissolved in 300 milliliters of methylene chloride, the solution cooled to 0-5 degrees centigrade and 50 grams of 2-chloroethyl isocyanate added dropwise while stirring. After standing for some time at zero degrees centigrade 115 grams of N-(2-chloroethyl)-N'-((2,2-diphenyl)-4-methyl-5-(dimethylamino)pentyl)urea crystallized which, after washing with diethyl ether, melted at 138-140 degrees centigrade.

25 Grams of the thus obtained urea-derivative were nitrosated with 7 grams of sodium nitrite in hydrochloric acid solution as described in Example 1, whereby 25 grams of N-(2-chloroethyl)-N'-(2,2-diphenyl-4-methyl-5-(dimethylamino)pentyl)-N-nitrosourea were obtained after crystallization from diisopropyl ether as yellow crystals which melted at 105-107 degrees centigrade.

EXAMPLE 4

N-(2-chloroethyl)-N'-(2,2-bis(4-fluorophenyl)-4-methyl-5-(dimethylamino)pentyl)-N-nitrosourea.

When Example 1 was carried out using 3-chloro-N,N,2-trimethylpropylamine instead of 3-chloro-N,N-dimethylpropylamine there were obtained as intermediates:

2,2-bis(4-fluorophenyl)-4-methyl-5-(dimethylamino)-pentanenitrile boiling at 165–175 degrees centigrade/0.2 mmHg.

$N^5,N^5$-dimethyl-2,2-bis(4-fluorophenyl)-4-methyl-1,5-pentanediamine, dioxalate. M.P.: 206–208 degrees centigrade.

N-(2-chloroethyl)-N'-(2,2-bis(4-fluorophenyl)-4-methyl-5-(dimethylamino)pentyl)urea. M.P.: 132–134 degrees centigrade.

By nitrosating the last mentioned urea-derivative N-(2-chloroethyl)-N'-(2,2-bis(4-fluorophenyl)-4-methyl-5-(dimethylamino)pentyl)-N-nitrosourea was obtained as a crystalline substance melting at 105–107 degrees centigrade.

In the same manner were the following nitrosourea derivatives of Formula I prepared:

N-(2-chloroethyl)-N'-(2,2-dicyclohexyl-5-(dimethylamino)pentyl)-N-nitrosourea maleate.
N-(2-chloroethyl)-N'-(2,2-bis(4-chlorophenyl)-5-(dimethylamino)pentyl)-N-nitrosourea.
N-(2-chloroethyl)-N'-(2,2-bis(1-fluorophenyl)-5-(dimethylamino)pentyl)-N-nitrosourea hydrochloride.
N-(2-chloroethyl)-N'-(2,2-bis(4-fluorophenyl)-5-(di-n-propylamino)pentyl)-N-nitrosourea.
N-(2-chloroethyl)-N'-(2,2-bis(4-fluorophenyl)-5-(N-piperidine)pentyl)-N-nitrosourea.
N-(2-chloroethyl)-N'-(2,2-bis(4-fluorophenyl)-5-(N-pyrrolidino)pentyl)-N-nitrosourea.
N-(2-chloroethyl)-N'-(2,2-bis(4-methylphenyl)-4-(dimethylamino)butyl)-N-nitrosourea pamoate.
N-(2-chloroethyl)-N'-(2,2-bis(4-trifluoromethylphenyl)-6-(N-morfoline)hexyl)-N-nitrosourea.
N-(2-chloroethyl)-N'-(2,2-bis(4-methoxyphenyl)-5-(dimethylamino)pentyl)-N-nitrosourea.
N-(2-chloroethyl)-N'-(2,2-bis(4-cyclohexylphenyl)-5-(dimethylamino)pentyl)-N-nitrosourea.

The following compounds have been tested in vivo in mice according to well recognized and reliable test methods aginst tumors:

N-(2-chloroethyl)-N'-(2,2-bis(4-fluorophenyl)-5-(dimethylamino)pentyl)-N-nitrosourea, called Lu-16-035 for short, and N-(2-chloroethyl)-N'-(2,2-diphenyl-4-methyl-5-(dimethylamino)pentyl)-N-nitrosourea, called LU-16-022 for short.

Lu 16-035 and Lu 16-022 were tested against the following tumors:

| | |
|---|---|
| P 388 lymphocytic leukemia | i.p. implanted |
| L 1210 lymphoid leukemia | i.p. and intracerebrally |
| Colon adenocarcinoma 26 | i.p. |
| Lewis lung carcinoma | i.v. |
| B 16 melanocarcinoma | i.p. |
| Ependymoblastoma | intracerebrally implanted |

In all these tumor systems, Lu-16-035 and Lu-16-022 have shown a significant to good effect. In some of the tumor systems the compounds in question have been compared with BCNU (1,3-bis(2-chloroethyl)-1-nitrosourea).

1. L 1210 i.p.

The drugs are administered intraperitonally (i.p.) in a single dose on day one after the implantation of the tumor in the mice.

| | Survivors/total on day 60 | |
|---|---|---|
| Lu 16-035 mg/kg | | |
| 200 | 0/7 | toxic dose |
| 100 | 4/7 | highest non-toxic dose |
| 50 | 3/7 | |
| 25 | 4/7 | |
| 12.5 | 0/7 | |
| BCNU mg/kg | | |
| 32 | 3/10 | highest non-toxic dose |
| 24 | 0/10 | |

2. Colon adenocarcinoma 26 i.p.

The drugs are administered i.p. on day 1.5 and 9 after the tumor implantation in the mice.

| | T/C % | Survivors/total on day 60 | |
|---|---|---|---|
| (T/C % = mean survival time of test animals in percent of control) | | | |
| Lu 16-035 mg/kg | | | |
| 100 | 41 | 2/10 | toxic dose |
| 50 | 255 | 9/10 | highest non-toxic dose |
| 25 | 255 | 9/10 | |
| 12.5 | 221 | 4/10 | |
| Lu 16-022 mg/kg | | | |
| 400 | 46 | 0/10 | toxic dose |
| 200 | 154 | 4/10 | toxic dose |
| 100 | 254 | 8/10 | highest non-toxic dose |
| 50 | 254 | 7/10 | |
| BCNU mg/kg | | | |
| 24 | 255 | 10/10 | highest non-toxic dose |
| 12 | 139 | 0/10 | |

3. B 16 Melanocarcinoma i.p.

The drugs are administered in one daily dose from day 1 to 9 after implantation of the tumor.

| | T/C % | Survivors/total on day 60 |
|---|---|---|
| Lu 16-035 mg/kg | | |
| 25 | 358 | 4/10 |
| 12.5 | 230 | 1/10 |
| 6.25 | 164 | 0/10 |
| Lu 16-022 mg/kg | | |
| 100 | 153 | 0/10 |
| 50 | 332 | 2/10 |
| 25 | 237 | 1/10 |

There is no direct comparison with other nitrosoureas but, it is reported in the literature that BCNU, CCNU and Me-CCNU can give at most a doubling of the survival time.

The compound N-(2-chloroethyl)-N'-(2,2-diphenyl-5-(dimethylamino)pentyl)-N-nitrosourea (Lu 15-132 for short) has so far only been tested against P 388 lymphocytic leukemia in mice. It has shown about the same activity and toxicity as Lu 16-035.

From these results it is seen, that Lu 16-035 and Lu 16-022 have better effects than BCNU on some tumors, and that they show a more favorable therapeutic index.

The compounds of Formula I and the pharmaceutically acceptable acid addition salts thereof may be administered to animals such as dogs, cats, horses, sheep or the like, including human beings, both orally and parenterally, and may be used for example in the form of tablets, capsules, powders, syrups or in the form of the usual sterile solutions for injection.

Most conveniently the compounds of Formula I are administered orally in unit dosage form such as tablets or capsules, each dosage unit containing a compound of Formula I or a pharmaceutically acceptable salt thereof in an amount of from about 1 to about 100 mg, most preferably, however, from about 10 to 50 calculated as the free amine.

The compounds of Formula I are usually administered in intervals of from four to ten weeks. The exact individual dosages in a particular case will, of course, be determined according to established medical principles under the direction of a physician. The dosage range for such cytostatic drugs is usually given as weight per squaremeter of body area and normally falls within from about 10 to about 200 milligrams per squaremeter of body area.

When preparing tablets, the active ingredient is for the most part mixed with ordinary tablet adjuvants such as corn starch, potato starch, talcum, magnesium stearate, gelatine, lactose, gums, or the like.

As previously stated, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bi-tartrates, embonates and maleates of the amines of Formula I. Other acids are likewise suitable and may be employed if desired. For example: Fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals by administering to a living animal body, including human beings, an adequate quantity of a compound of Formula I or a non-toxic acid addition salt thereof. An adequate quantity would be from about 5 mg to about 100 mg per squaremeter of body area in each unit dosage, and from about 15 milligrams to about 300 milligrams/squaremeter of body area every fourth to sixth week.

It is to be understood that the invention is not limited to the exact details of operation or exact compound or compositions shown and described, as obvious modifications and equivalents will be apparent to one skilled in the art.

We claim:

1. A compound of the formula:

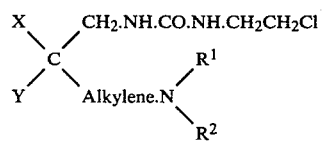

wherein X and Y are the same or different and are each selected from the group consisting of phenyl and phenyl substituted with halogen, "alkylene" is an alkylene group having one to four carbon atoms inclusive, and $R^1$ and $R^2$ are the same or different and are each lower alkyl having one to four carbon atoms inclusive, and acid addition salts thereof.

2. A compound according to claim 1 of the formula:

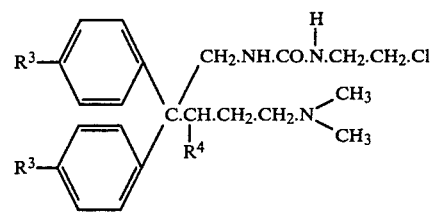

wherein $R^3$ is selected from the group consisting of hydrogen and fluorine and $R^4$ is selected from the group consisting of hydrogen and methyl.

3. N-(2-chloroethyl)-N'-(2,2-bis(4-fluorophenyl)-5-(dimethylamino)pentyl) and acid addition salts thereof.

4. N-(2-chloroethyl)-N'-((2,2-diphenyl)-5-(dimethylamino)pentyl) and acid addition salts thereof.

5. N-(2-chloroethyl)-N'-(2,2-bis(4-fluorophenyl)-4-methyl-5-(dimethylamino)pentyl) and acid addition salts thereof.

6. N-(2-chloroethyl)-N'-(2,2-diphenyl-4-methyl-5-(dimethylamino)pentyl)urea and acid addition salts thereof.

* * * * *

UNITED STATES PATENT AND TRADEMARK OFFICE
CERTIFICATE OF CORRECTION

PATENT NO. : 4,384,140
DATED : May 17, 1983
INVENTOR(S) : Peter Bregnedal and Jørn L. M. Buus It is certified that error appears in the above—identified patent and that said Letters Patent is hereby corrected as shown below:

Col. 4, line 32; "(2,2-diphenyl)-" should read -- ((2,2-diphenyl)- --

Col. 8, line 50; insert -- urea -- before "and"
Col. 8, line 52; insert -- urea -- before "and"
Col. 8, line 54; insert -- urea -- before "and"

Signed and Sealed this

Ninth Day of August 1983

[SEAL]

Attest:

GERALD J. MOSSINGHOFF

Attesting Officer   Commissioner of Patents and Trademarks